United States Patent
Kato et al.

(10) Patent No.: US 9,192,527 B2
(45) Date of Patent: Nov. 24, 2015

(54) ABSORBENT ARTICLE

(75) Inventors: Nobuyuki Kato, Kanonji (JP); Tatsuya Tamura, Kanonji (JP); Toshihisa Hayashi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 224 days.

(21) Appl. No.: 13/824,513

(22) PCT Filed: Sep. 27, 2011

(86) PCT No.: PCT/JP2011/072716
§ 371 (c)(1),
(2), (4) Date: Mar. 18, 2013

(87) PCT Pub. No.: WO2012/043851
PCT Pub. Date: Apr. 5, 2012

(65) Prior Publication Data
US 2013/0184665 A1    Jul. 18, 2013

(30) Foreign Application Priority Data
Sep. 30, 2010   (JP) ................................. 2010-223059

(51) Int. Cl.
*A61F 13/15* (2006.01)
*A61F 13/53* (2006.01)
*A61F 13/538* (2006.01)
*A61F 13/47* (2006.01)
*A61F 13/536* (2006.01)

(52) U.S. Cl.
CPC ........... *A61F 13/538* (2013.01); *A61F 13/4704* (2013.01); *A61F 13/536* (2013.01)

(58) Field of Classification Search
CPC ..... A61F 13/53; A61F 13/534; A61F 13/535; A61F 13/5355; A61F 13/536; A61F 13/533; A61F 2013/530007; A61F 2013/530014; A61F 2013/520021; A61F 2013/530029; A61F 2013/530036; A61F 2013/53734; A61F 2013/53739
USPC ..................... 604/378, 379, 380, 383, 385.04
See application file for complete search history.

(56) References Cited

U.S. PATENT DOCUMENTS

| 2003/0187417 | A1 | 10/2003 | Kudo et al. |
| 2004/0243084 | A1 | 12/2004 | Yoshimasa et al. |
| 2005/0054253 | A1 | 3/2005 | Minoguchi et al. |

FOREIGN PATENT DOCUMENTS

| JP | 2003-291234 A | 10/2003 |
| JP | 2004-141619 A | 5/2004 |
| JP | 2004-229767 A | 8/2004 |
| JP | 2004-298411 A | 10/2004 |
| JP | 2004-350726 A | 12/2004 |
| WO | 2012118214 A1 | 9/2012 |

OTHER PUBLICATIONS

International Search Report corresponding to PCT/JP2011/072716, dated Dec. 13, 2011.

*Primary Examiner* — Jacqueline Stephens
(74) *Attorney, Agent, or Firm* — Hauptman Ham, LLP

(57) ABSTRACT

An absorbent article includes a liquid-permeable top sheet, a liquid-impermeable back sheet provided at a location opposing the top sheet, an absorbent provided between the top sheet and the back sheet, and a side sheet provided on both sides of the top sheet in the widthwise direction and having an area that overlaps the top sheet and the absorbent, wherein the absorbent contains an airlaid layer and a crushed pulp layer, the crushed pulp layer is provided on the top sheet side, the airlaid layer is provided on the back sheet side, and the absorbent article has a plurality of indentations formed by pin-embossing the top sheet, the side sheet and the absorbent, and a plurality of indentations formed by pin-embossing the top sheet and the absorbent.

23 Claims, 8 Drawing Sheets

(a)

(b)

(a)

(b)

(a)

(b)

(c)

(a)

(b)

(a)

(b)

(a)

(b)

(c)

ABSORBENT ARTICLE

RELATED APPLICATIONS

The present application is a National Phase International Application Number PCT/JP2011/072716, filed Sep. 27, 2011, and claims priority from Japanese Application Number 2010-223059, filed Sep. 30, 2010.

TECHNICAL FIELD

The present invention (disclosure) relates to an absorbent article such as a sanitary napkin, panty liner, incontinence pad or incontinence liner, and more particularly, to a thin absorbent article.

BACKGROUND ART

Absorbent articles are generally required to be as thin as possible in order to prevent a sweltering sensation when worn, especially if used in environments at high temperatures. In order to make absorbent articles as thin as possible, absorbent articles are known in the prior art which have an absorbent layer composed of an airlaid non-woven fabric, with a plurality of indentations, formed by embossing, that extend from a surface layer of the absorbent article to the absorbent layer (see, for example, Patent Document 1).

CITATION LIST

Patent Literature

[Patent Literature 1] Japanese Unexamined Patent Publication No. 2003-291234

SUMMARY OF THE INVENTION

Technical Problem

The inventor(s) have recognized that airlaid non-woven fabric, in which adjacent fibers are joined together, is more resistant to twisting than crushed pulp typically used for the absorbent layer even after a long-term use. However, an absorbent layer that uses airlaid non-woven fabric might exhibit low cushioning with respect to the skin of the wearer. An object of the present invention is to provide an absorbent article in which a plurality of indentations are formed by embossing extending from a surface sheet to an absorbent, in which the absorbent of the absorbent article is resistant to twisting even after long-term use and has favorable cushioning with respect to the skin of the wearer.

Solution of Problem

The present invention employs the following configuration to solve the aforementioned problems.

Namely, the present invention is an absorbent article provided with a liquid-permeable top sheet, a liquid-impermeable back sheet provided at a location opposing the top sheet, an absorbent provided between the top sheet and the back sheet, and a side sheet provided on each side of the top sheet in the widthwise direction having an area that overlaps the top sheet and the absorbent, wherein the absorbent contains an airlaid layer, formed by joining fibers with a binder, and a crushed pulp layer, the crushed pulp layer is provided on the top sheet side of the absorbent, the airlaid layer is provided on the back sheet side of the absorbent, and the absorbent article has a plurality of compressed pin shaped indentations extending through the side sheet, the top sheet and into the absorbent in the thickness direction and a plurality of compressed pin shaped indentations extending through the top sheet into the absorbent in the thickness direction by pin embossing.

The term "top sheet" is used in its normal sense in this art to mean the permeable layer on top of the absorbent, however it need not be the top most layer over the total article, for example the side sheets may be on top of the top sheet where they overlap the top sheet.

Advantageous Effects of the Invention

According to the present invention, an absorbent article can be provided in which the absorbent is resistant to twisting even when the absorbent article is worn for a long period of time, and which has favorable cushioning with respect to the skin of the wearer.

DESCRIPTION OF EMBODIMENTS

The following provides an explanation of an absorbent article of some embodiments of the present invention with reference to the drawings. The absorbent article of an embodiment of the present invention is a thin sanitary napkin.

Figure 1:
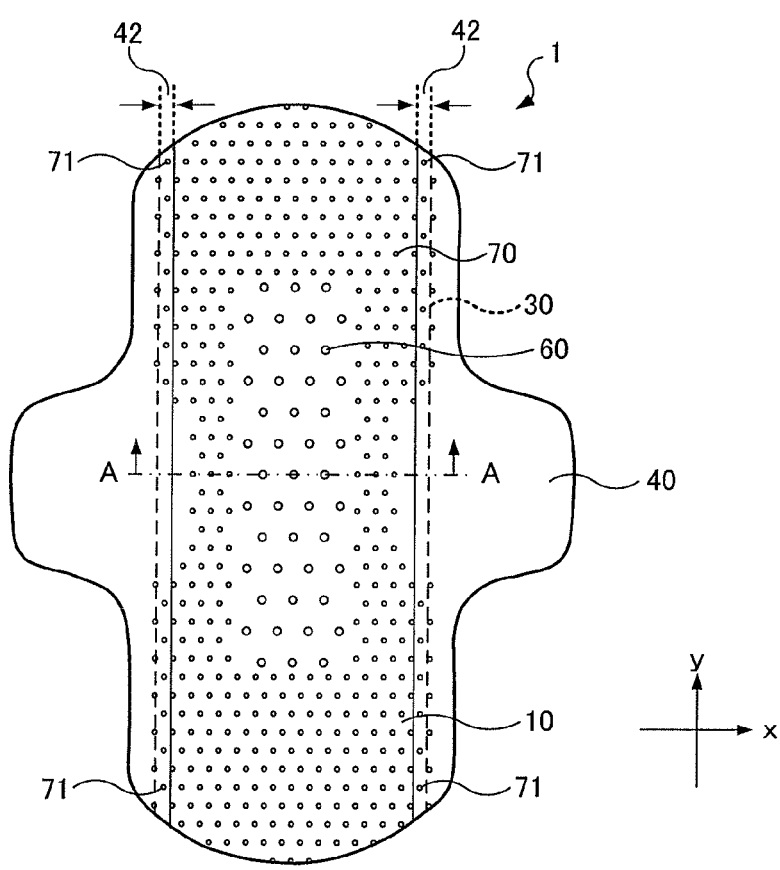
FIG. 1 is a drawing for explaining an absorbent article of an embodiment of the present invention.
Figure 1:
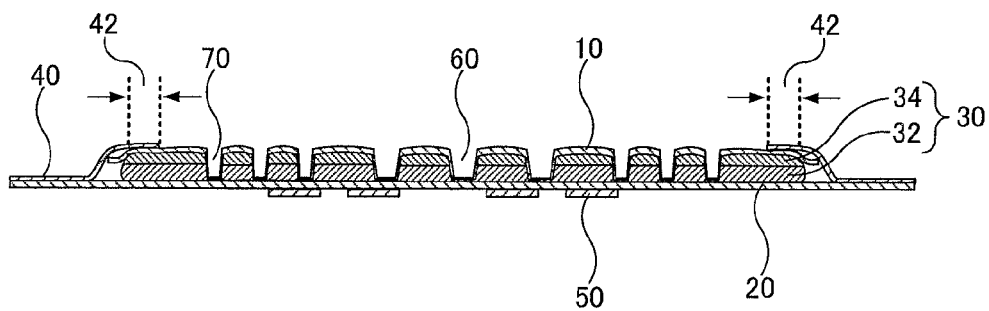

FIG. 1 is a drawing explaining an absorbent article of an embodiment of the present invention. FIG. 1(a) is an overhead view of an absorbent article in an embodiment of the present invention, and FIG. 1(b) is a cross-sectional view taken along line A-A of FIG. 1(a). An absorbent article 1 in an embodiment of the present invention is provided with a liquid-permeable top sheet 10, a liquid-impermeable back sheet 20 opposite to the top sheet 10, an absorbent 30 provided between the top sheet 10 and the back sheet 20, and side sheets 40 which are provided on both sides of the top sheet 10 in the widthwise direction which protrude in the widthwise direction (denoted by arrow X in FIG. 1). The side sheets 40 illustrated have central wing portions extending in the widthwise direction, but in some embodiments these may not be required.

A pressure-sensitive adhesive portion 50 may be provided on an outer surface (garment-facing side) of the back sheet 20, i.e., the side opposite from the skin-facing side of the back sheet 20 that opposes the top sheet 10.

The absorbent 30 contains an airlaid layer 32, which may be formed by joining fibers with a binder, and a crushed pulp layer 34. The airlaid layer is provided on the back sheet side (or garment-facing side) of the absorbent 30, while the crushed pulp layer 34 is provided on the top sheet side (or skin-facing side) of the absorbent 30. The top sheet 10 and the absorbent 30 have a plurality of indentations 60 and 70 extending from the top sheet 10 through the crushed pulp layer 34 and into the airlaid layer 32 of the absorbent 30. These may be formed by compressing in the thickness direction by pin embossing. Pin embossing means embossing that is carried out by using pins provided in a roller.

In addition, the top sheet 10, the side sheet 40 and the absorbent 30 overlap in the lateral areas of the absorbent article 1, i.e., within the range of denoted by reference symbols 42 of FIG. 1. Thus, a plurality of indentations 71 in the lateral areas of the range of reference symbols 42 are indentations that extend through the side sheets 40 and top sheet 10, through the crushed pulp layer 34 to the airlaid layer 32 of the absorbent 30. In some embodiments, except for the position and the extension through the side sheet 40, the indentations 71 are similar to the indentations 70.

In an alternative embodiment, the top sheet 10 could be placed on top of the side sheets 40.

In FIG. 1, the widthwise direction of the absorbent article 1 is the direction of the x axis, while the lengthwise direction is the direction of the y axis. Similarly, the widthwise direction of the absorbent article 1 is the direction of the x axis and the lengthwise direction is the direction of the y axis in FIGS. 2, 5, 6.

The top sheet 10 is a sheet that contacts the skin of a wearer when the absorbent article is worn. Although a non-woven fabric is mainly used for the top sheet 10, there are no limitations on materials of the top sheet 10, provided that it is a sheet that allows liquid to pass through. For example, a woven fabric, plastic sheet or mesh sheet may also be used for the top sheet 10. A natural fiber or chemical fiber can be used for the non-woven fabric used in the top sheet 10. Examples of natural fibers used in the top sheet 10 include cellulose fibers such as crushed pulp or cotton. Examples of chemical fibers used in the top sheet 10 include regenerated cellulose fibers such as rayon or fibril rayon, semi-synthetic cellulose fibers such as acetate or triacetate, thermoplastic hydrophobic fibers, and thermoplastic hydrophilic fibers subjected to hydrophilic treatment. Examples of thermoplastic hydrophobic fibers include monofilaments such as polyethylene (PE), polypropylene (PP) or polyethylene terephthalate (PET), and composite fibers such as fibers obtained by graft polymerization of polyethylene and polypropylene and fibers having a core-sheath structure.

A dry method (such as a carding, spun bonding, melt blowing or air laying) or a wet method can be used to produce the non-woven fabric used in the top sheet 10. Both a wet method and a dry method may also be combined. In addition, the non-woven fabric used in the top sheet 10 may also be produced using a method such as thermal bonding, needle punching or chemical bonding. However, the method used to produce the non-woven fabric is not limited to the above methods, and may be produced by other methods as well.

Spun lace formed into the shape of a sheet by hydroentangling, for example, can also be used for the non-woven fabric used in the top sheet 10. In addition, a non-woven fabric having surface irregularities in the upper layer thereof, or a corrugated non-woven fabric in which fabric weight unevenness is provided in the non-woven fabric by applying air during web formation, can also be used for the non-woven fabric used in the top sheet 10. In the case of forming surface irregularities in the non-woven fabric, dispersion of liquid over the surface of the top sheet 10 can be reduced before liquid passes through the top sheet 10.

The back sheet 20 is a sheet for inhibiting leakage of liquid absorbed with the absorbent 30 from the wearer to the outside. A film composed mainly of polyethylene or polypropylene and the like, a porous resin film, or a sheet obtained by joining a porous resin film to a non-woven fabric such as spun bonded fabric or spun lace can be used for the back sheet 20. The back sheet 20 preferably has flexibility to a degree that does not cause discomfort to the wearer when worn.

The absorbent 30 extends to both ends of the absorbent article 1 in the lengthwise direction in some embodiments. In Further embodiments, the absorbent 30 is not required to reach both ends of the absorbent article 1 in the lengthwise direction.

The airlaid layer 32 of the absorbent 30 is composed of an airlaid non-woven fabric. The airlaid non-woven fabric is produced by, for example, dispersing a mixture of hydrophilic fibers and thermoplastic resin fibers in air, passing through a screen having a metal mesh and pores, dropping onto a wire traveling there below, spraying with a water-soluble binder, and carrying out heat treatment to heat-seal the thermoplastic resin fibers with the hydrophilic fibers. Furthermore, the surfaces of the thermoplastic resin fibers may also be adhered to the hydrophilic fibers followed by heat-sealing the thermoplastic resin fibers with the hydrophilic fibers without using a water-soluble binder. In this case, the surface of the thermoplastic resin fibers serves as a binder that heat-seals the thermoplastic resin fibers to the hydrophilic fibers.

For example, a non-woven fabric, obtained by spraying pulp serving as hydrophilic fibers and composite thermoplastic fibers (2.2 dtex, fiber length: 5 mm), comprising a core consisting of PET (polyethylene terephthalate) and a sheath consisting of PE (polyethylene), with a vinyl alcohol-based emulsion adhesive followed by adhering by heat treatment, can be used for the airlaid non-woven fabric.

One type or a mixture of two or more types of wood pulp, rayon, acetate rayon, natural cellulose fibers other than pulp, mercerized pulp and crosslinked pulp are used for the hydrophilic fibers. In addition to the aforementioned composite thermoplastic resin fibers, composite thermoplastic resin fibers comprising PP (polypropylene) for the core and PE for the sheath, or monofilaments of PE, PP or PET, can be used for the heat-sealable thermoplastic resin fibers.

The crushed pulp layer 34 of the absorbent 30 is a layer mainly containing crushed pulp or a layer composed exclusively of crushed pulp. For example, the crushed pulp is produced by crushing a pulp sheet with a crushing machine. The crushed pulp is not joined together with an adhesive and the like.

The crushed pulp layer 34 may be joined to the airlaid layer 32 by a hot melt adhesive.

Furthermore, the absorbent 30 may also have another layer between the airlaid layer 32 and the crushed pulp layer 34. In addition, the absorbent 30 may also have another layer on the back sheet side (or garment-facing side) of the airlaid layer 32 opposite from the crushed pulp layer 34.

As a result of providing the airlaid layer 32 on the back sheet side of the absorbent 30 and providing the crushed pulp layer 34 on the top sheet side of the absorbent 30, the absorbent 30 can be formed to have favorable cushioning and durability, the crushed pulp layer 34 providing a particularly good cushioning effect close to the wearer with the airlaid layer 32 being less easy to twist.

The top sheet 10 is joined to the absorbent 30 using, for example, a hot melt adhesive. Examples of coating patterns of the hot melt adhesive on the top sheet 10 or the absorbent 30 include a parallel line pattern in which parallel lines extending in the lengthwise direction are arranged in parallel at prescribed intervals in the widthwise direction, a band pattern in which bands extending in the lengthwise direction are arranged in parallel in the widthwise direction, a wavy pattern in which wavy lines having an amplitude in the widthwise direction and extending in the lengthwise direction are arranged in parallel in the widthwise direction, or a spiral pattern in which spirals extending in the lengthwise direction are arranged in the widthwise direction. The coated basis weight of the adhesive is preferably 1 to 10 g/m$^2$. As a result, the hot melt adhesive can be coated over the entire top sheet 10 or absorbent 30, and a hard texture of the absorbent article 1 due to the presence of the hot melt adhesive can be reduced, thereby resulting in a favorable sensation during use of the absorbent article 1.

The side sheets 40 inhibit leakage of liquid flowing from a wearer to the outside in the widthwise direction of the absorbent article 1. For example, a material similar to that of the back sheet 20 is used for the side sheet 40. In addition, in order to prevent liquid of the wearer from flowing to the outside as a result of passing over the side sheets 40, the material of the side sheet 40 is preferably hydrophobic or water-repellent. A spun bond non-woven fabric or spunbond/meltblown/spundbond (SMS) non-woven fabric, for example, can be used for the side sheets 40. Since the side sheets 40 contact the skin of the wearer, an air-through non-woven fabric is preferably used.

The peripheral edges of the top sheet 10, the back sheet 20 and the side sheet 40 may be joined by using a method such as heat embossing, ultrasonic processing or hot melt adhesive or a combination thereof.

The indentations 60 and 70 formed in the top sheet 10 and the absorbent 30, as well as the indentations 70 formed in the top sheet 10, the absorbent 30 and the side sheet 40, can be formed by pin embossing as previously described. The indentations 60 and 70 are arranged in a staggered pattern. The shape of the openings of the indentations 60 and 70 in the planar direction (i.e., in plan view) is circular. Furthermore, the openings of the indentations may have two or more different shapes in the planar direction. As a result, rigidity and thickness of the absorbent 30 of the absorbent article 1, in which indentations are formed by embossing may be further controlled. For example, the shape of the openings in the planar direction in a central portion of an absorbent article may be square, while the shape of indentations in the planar direction of a peripheral portion of the absorbent article may be circular. Furthermore, the shape of the indentations of the absorbent article is not limited to being square or circular, but may be any shape, e.g., a polygon such as a rectangle or triangle, or a star, oval. The diameter of an indentation in plan view is defined herein as the diameter of the smallest circle that completely contains the indentations, in plan view, at the surface. In addition, the indentations of a single absorber may have at least two different sizes in the planar direction and/or at least two different shapes in the planar direction. As a result, cushioning and thickness of an absorbent of an absorbent article in which indentations are formed by embossing can be further controlled.

In the case the absorbent article 1 is less than 4 mm thick, the distance in the planar direction (xy direction) between two adjacent indentations 60 or 70 is preferably between 3 to 20 mm. If the distance in the planar direction between the two adjacent indentations 60 or 70 is less than 3 mm, cushioning of the absorbent article 1 may be weakened and the absorbent article 1 may become hard. If the distance in the planar direction between the two adjacent indentations 60 or 70 exceeds 20 mm, the crushed pulp easily becomes unevenly distributed between the indentations 60 and 70, and may result in twisting of the absorbent 30. In addition, since the contact surface area of the absorbent article 1 with the skin of a wearer increases, the wearer may experience a sensation of stickiness from the absorbent article 1 when the absorbent 30 has absorbed a liquid.

In some embodiments where the absorbent article 1 is less than 4 mm thick, the diameter in the planar direction of the indentations 60 and 70 (diameter of the maximum opening of the indentations 60 and 70) is preferably from 0.5 to 6.0 mm. If the diameter in the planar direction of the indentations 60 and 70 is less than 0.5 mm, the crushed pulp layer 34 may be prevented from being adequately fixed to the airlaid layer 32 by the indentations 60 and 70, thereby the prevention of twisting of the absorbent of the absorbent article 1 may not be achievable. If the diameter in the planar direction of the indentations 60 and 70 exceeds 6.0 mm, the size of the rigid portion that contacts the skin increases, which may cause a wearer to experience a hard sensation when body pressure is applied to the absorbent article 1.

In order to allow the overall absorbent article 1 to have a certain degree of flexibility as well as durability to prevent the occurrence of twisting, the ratio of the total surface area of all indentations 60 and 70 in plan view is preferably 3 to 30% and more preferably 5 to 10% based on the total surface area of the absorbent article 1 in the planar direction.

In order to suppress or eliminate discomfort in the crotch of a wearer, the width of the area of the absorbent article 1 where the indentations 60 and 70 are formed is narrower roughly in or in the center in the lengthwise direction.

As shown in FIG. 1, the side sheets 40 have indentations 71 formed by compressing the top sheet 10, the side sheets 40 and the absorbent 30 in the thickness direction in the vicinity of the ends of the areas 42 in the lengthwise direction that overlap the top sheet 10 and the absorbent 30.

As shown in FIG. 1, the indentations 60 and 70 provided in the absorbent article 1 have two different sizes in the planar direction. In particular, the size in the planar direction of the indentations 60 in a central portion of the absorbent article 1 in an area roughly in or in the center in the lengthwise and widthwise directions is preferably larger than the size in the planar direction of the indentations 70 located in a peripheral portion around the central portion. In addition, the number of indentations 60 per unit surface area in the central portion of the absorbent article 1 is preferably less than the number of indentations 70 per unit surface area in the peripheral portion around the central portion.

Figure 2:
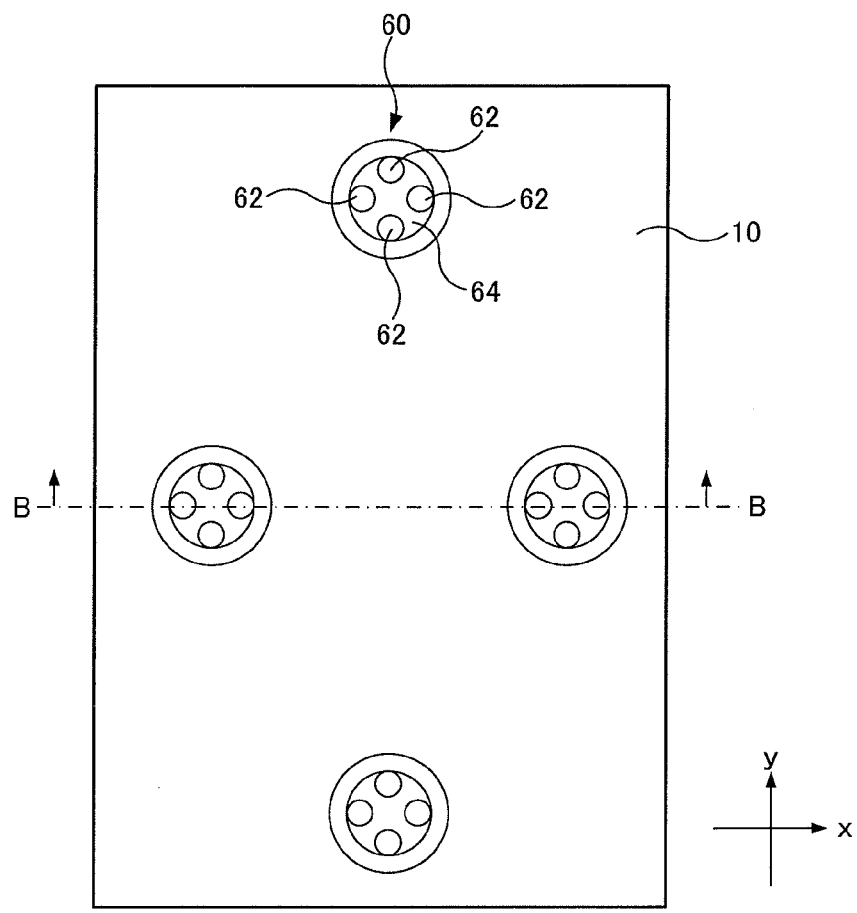
FIG. 2 is a drawing for explaining indentations in a central portion of an absorbent article of an embodiment of the present invention.
Figure 2:
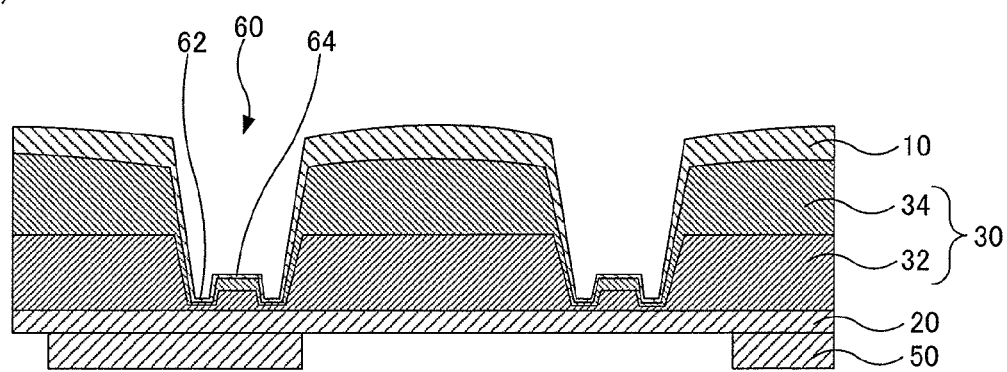

FIG. 2(a) is an overhead view of the indentations 60 in the central portion of the absorbent article 1, while FIG. 2(b) is a cross-sectional view taken along line B-B in FIG. 2(a). As shown in FIG. 2, the indentations 60 in the central portion of the absorbent article 1 includes portions 62 which are compressed more than less compressed portions 64 and thus portions 62 have a greater depth in the thickness direction. Four more compressed portions 62 are provided in the single indentations 60. The shape in the planar direction of the more compressed portions 62 is circular. Furthermore, more compressed portions 62 and less compressed portions 64 may also be provided in the indentations 70 and 71 of the peripheral portion of the absorbent article 1. In addition, the shape in the planar direction of the more compressed portions 62 is not limited to being circular, but may be any shape, e.g., a polygon such as a quadrangle or rectangle, or a star, etc. In addition, the number of more compressed portions 62 provided in a single indentation is not limited to four, but may be 1, 2, 3 or 5 or more.

The provision of more compressed portions 62 and less compressed portions 64 in the indentations permits a density gradient to be formed at the bottom of the indentations which acts to improve the absorption of liquid at the bottom of the indentations 60 and 70.

As shown in FIG. 2, although the top sheet 10 is present in the bottom portions of the indentations 60 of the central portion of the absorbent article 1, the top sheet 10 in some embodiments is not required to be present in the bottoms of some or all of the indentations 60. In addition, the top sheet 10 in some embodiments is also not required to be present in the bottom portions of some or all of the indentations 70 of the peripheral portion of the absorbent article 1.

The pressure-sensitive adhesive portion 50 is a pressure-sensitive adhesive layer for fixing the absorbent article 1 to an undergarment such as underpants that contacts the garment-facing side of the back sheet 20. The pressure-sensitive adhesive portion 50 is formed by coating a pressure-sensitive adhesive on the surface of the back sheet 20 contacted by the skin, or by coating a pressure-sensitive adhesive onto a packaging sheet for which the entire surface thereof has been subjected to release treatment, followed by transferring the coated pressure-sensitive adhesive onto the surface of the back sheet 20 contacted by the skin. The shape in the planar direction of the pressure-sensitive portion 50 is that of a rectangle that extends in the lengthwise direction of the absorbent article 1. The pressure-sensitive adhesive portion is arranged in rows in the widthwise direction of the absorbent article 1. The surface of the pressure-sensitive portion 50 is covered with a release sheet not shown prior to use of the absorbent article 1.

Examples of the pressure-sensitive adhesive for forming the pressure-sensitive portion 50 include thermoplastic polymers such as a styrene-based block polymer, natural resin-based or synthetic resin-based adhesion-imparting resins, and plastic materials such as paraffin-based oils. Examples of styrene-based block polymers used for the pressure-sensitive portion 50 include styrene-ethylene-butadiene-styrene (SEBS) block copolymer, styrene-butadiene-styrene (SBS) block copolymer, styrene-isoprene-styrene (SIS) block copolymer and styrene-ethylene-propylene-styrene (SEPS) block copolymer. Examples of natural resin-based adhesion-imparting resins include terpene-based resins such as copolymers of $\alpha$-pinene, $\beta$-pinene or dipentene, rosin-based resins such as gum rosin, tall oil rosin or wood rosin, and hydrogenation products or esters thereof. In addition, examples of synthetic resin-based adhesion-imparting resins include aliphatic (C5) petroleum resins, aromatic (C9) petroleum resins, copolymer-based petroleum resins, hydrogenated petroleum resins, DCPD-based petroleum resins and pure monomer-based petroleum resins. In addition, examples of plastic materials include paraffin oils that decrease viscosity, naphthene oils that increase tackiness, and aromatic oils that decrease cohesion or impart color or odor.

The coated basis weight of the pressure-sensitive adhesive of the pressure-sensitive adhesive portion 50 is 10 to 100 g/m$^2$ and preferably 20 to 50 g/m$^2$. If the basis weight is less than 10 g/m$^2$, the adhesive strength of the absorbent article 1 may end up weakening, the absorbent article 1 may end up not attaching to an undergarment such as underpants, the absorbent article 1 may end up falling or shifting during use, or may end up causing discomfort for the wearer. In addition, if the coated amount is greater than 100 g/m$^2$, the adhesive strength of the absorbent article 1 may end up being excessively strong, the absorbent article 1 may be torn when the absorbent article 1 is peeled from an undergarment such as underpants, or a portion of the absorbent article 1 may become attached to an undergarment such as underpants and be unable to be peeled off, thereby making this undesirable.

Figure 3:
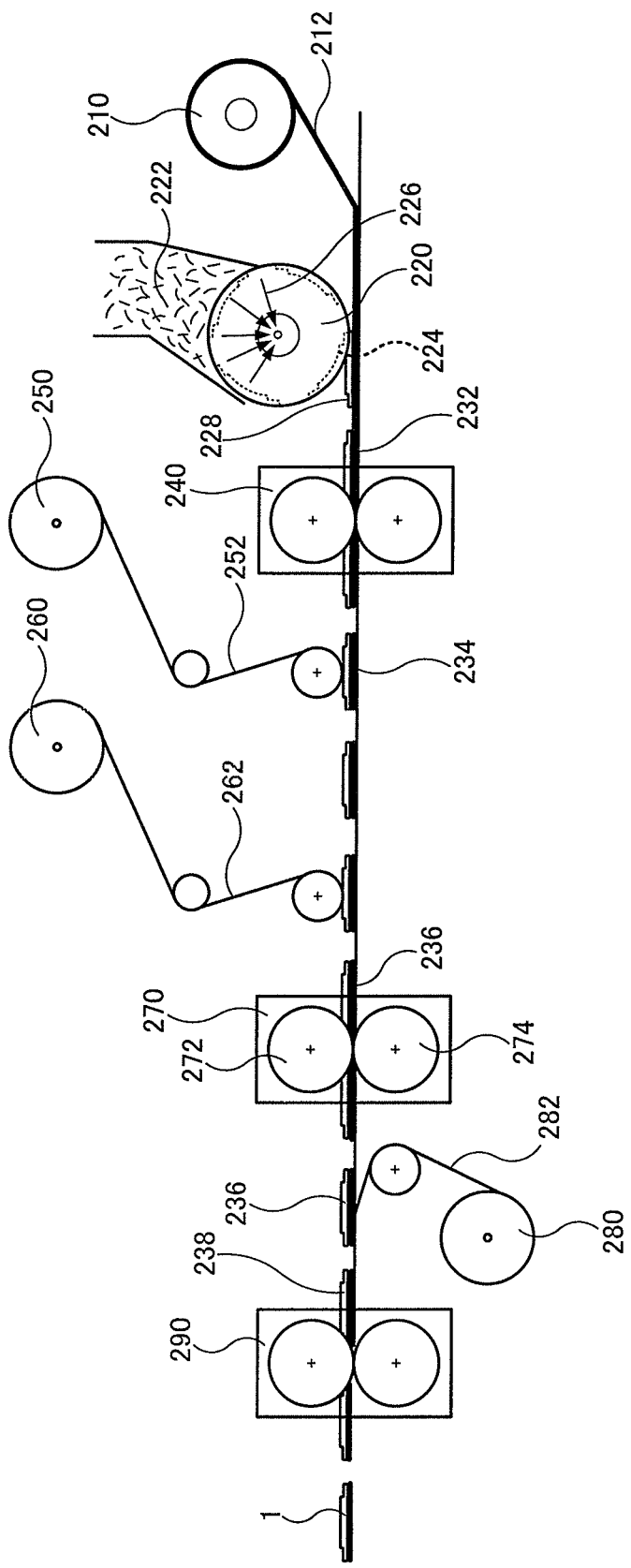
FIG. 3 is a drawing for explaining a production method and equipment of an absorbent article in an embodiment of the present invention.

Next, an explanation is provided of a production method and equipment of the absorbent article 1 in an embodiment of the present invention with reference to FIG. 3. A band-shaped airlaid non-woven fabric 212 is fed from an airlaid non-woven fabric roller 210 on which is wound the airlaid non-woven fabric 212. Crushed pulp 222 is fed from a crushed pulp supply device not shown to a pattern drum 220. Indentations 224 are formed in a shape that packs the crushed pulp on the outer periphery of the pattern drum 220. Suction 226 is generated within the pattern drum 220, and the crushed pulp 222 fed to the pattern drum 220 is suctioned into the indentations 224 and compressed. A crushed pulp layer 228 formed within the indentations 224 is layered onto the airlaid non-woven fabric 212 and joined with a hot-melt pressure-sensitive material resulting in the production of an absorbent 232 composed of the airlaid non-woven fabric 212 and the crushed pulp layer 228. The absorbent 232 is cut into individual absorbents 234 by making cuts to the front and back of the absorbent 232 with an absorbent front and back-cutting cutter 240.

Figure 4:
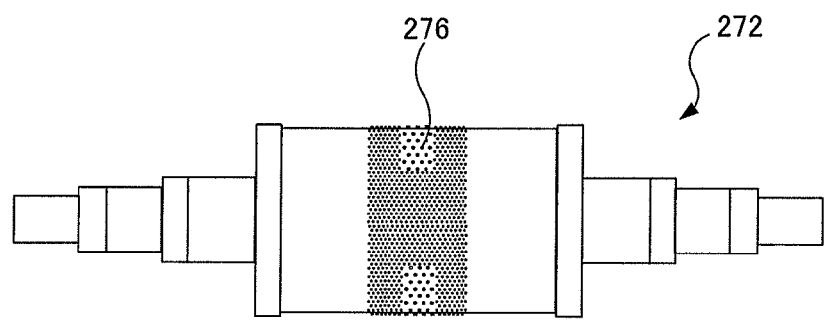
FIG. 4 is a drawing for explaining an upper roller and a lower roller of an embossing device used when producing an absorbent article in an embodiment of the present invention.
Figure 4:
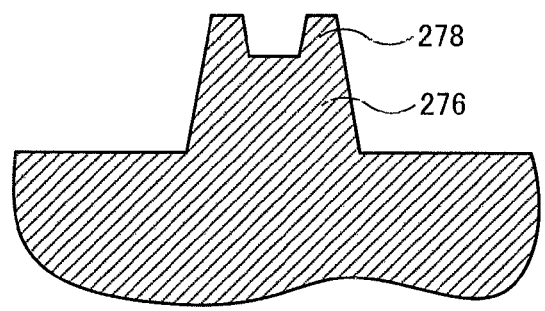
Figure 4:
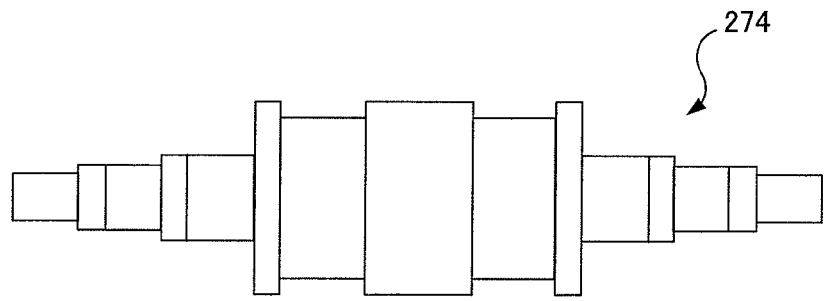

Each of the absorbents 234 is covered with a top sheet 252 supplied from a top sheet roller 250, and the top sheet 252 is joined to the absorbent 234 by using a hot-melt adhesive. Moreover, side sheets 262 are fed from a side sheet roller 260 and arranged on both sides of the top sheet 252 so as to overlap with respective side portions of the top sheet 252. Next, the absorbent 234 is compressed in the thickness direction using an embossing device 270 to form a plurality of indentations extending from the top sheet 252 to inside the absorbent 234 and a plurality of indentations extending from the side sheets 262 to the absorbent 234 through the top sheet 252 in a laminate 236 comprised of the side sheet 262, the top sheet 252 and the absorbent 234. The following provides an explanation of an upper roller 272 and a lower roller 274 of the embossing device 270 with reference to FIG. 4. As shown in FIG. 4($a$), pins 276 are provided on the upper roller 272 at locations corresponding to the indentations 60 and 70 (see FIG. 1) provided in the absorbent article 1. The shape of the pins is flat with the exception of a conical tip. As shown in FIG. 4($b$), projections 278 are provided on the tips of the pins 276 corresponding to the indentations 60 of the central portion of the absorbent article 1 in order to form the highly compressed portions 62 (see FIG. 2) of the indentations 60. The diameter of the tips of the pins 276 is preferably within the range of 0.5 to 6.0 mm, and more preferably within the range of 1.0 to 2.5 mm in consideration of the balance between rigidity and flexibility of the absorbent article 1. If the diameter of the tips of the pins 276 is less than 0.5 mm, the laminate 236 is unable to be adequately compressed, while if the diameter is greater than 6.0 mm, the laminate 236 is compressed excessively, which may end up causing the laminate 236 to be excessively hard. As shown in FIG. 4($c$), projections such as pins are not formed on the lower roller 274.

A back sheet 282 fed from a back sheet roller 280 shown in FIG. 3 is adhered by overlapping the surface of the embossed laminate 236 on the side opposite from the top sheet side to form a continuum 238 of the absorbent article. The continuum 238 of the absorbent article is cut into the shape of an absorbent article using a cutter 290 to produce the absorbent article 1. Furthermore, the individual absorbents 234 are obtained by cutting the adsorbent 232 in the front and back with the absorbent front and back-cutting cutter 240 in the aforementioned steps. However, individual absorbents may also be obtained as a result of cutting the continuum 238 of the absorbent article into the shape of absorbent articles by using the cutter 290 instead of using the absorbent front and back-cutting cutter 240.

The absorbent article 1 of an embodiment of the present invention as described above demonstrates one or more of the actions and effects indicated below.

(1) The absorbent article 1 is provided with the liquid-permeable top sheet 10, the liquid-impermeable back sheet 20 provided at a location opposing the top sheet 10, the absorbent 30 provided between the top sheet 10 and the back sheet 20, and a side sheet 40 provided on each side of the top sheet 10 in the widthwise direction, each having an area that overlaps the top sheet 10 and the absorbent 30, wherein the absorbent 30 contains the airlaid layer 32, formed by joining fibers with a binder, and the crushed pulp layer 34, the crushed pulp layer 34 is provided on the top sheet side of the absorbent 30, the airlaid layer 32 is provided on the back sheet side of the absorbent 30, and the absorbent article 1 has a plurality of the indentations 71 formed by compressing the top sheet 10, the side sheet 40 and the absorbent 30 in the thickness direction by pin embossing, and a plurality of the indentations 60 and 70 formed by compressing the top sheet 10 and the absorbent 30 in the thickness direction by pin embossing. As a result, the absorbent article 1 can be provided in which the absorbent 30 is unlikely to twist or tear even if a wearer has moved for a long period of time after the absorbent article 1 has absorbed liquid, and which has favorable cushioning of the skin of the wearer. In addition, since crushed pulp in the crushed pulp layer 34 is able to respectively move easily, the pins 276 of the embossing device 270 easily penetrate the absorbent 232, thereby making it possible to easily form the indentations 60 and 70 by pin embossing.

(2) At least a portion of the indentations 60 among the plurality of indentations 60 and 70 include the more compressed portions 62 and the less compressed portions 64 having different depths in the thickness direction, and the depth in the thickness direction of the more compressed portions 62 is greater than the depth in the thickness direction of the less compressed portions 64. As a result, a density gradient can be formed in the absorbent 30 at the bottoms of the indentations 60, thereby improving absorption of liquid of a wearer of the absorbent article 1. In addition, since the shape of the pins 276 of the upper roller 272 of the embossing device 270 given a shape that facilitates penetration of the absorbent 30, a durable absorbent article 1 can be produced. The thickness dimension of the more compressed portions 62 and the less compressed portions 64 can be measured by, for example, using the measurement method described below. After immersing and freezing a sample absorbent article in liquid nitrogen, the frozen sample is cut with a razor blade and returned to room temperature followed by measuring the thickness dimension thereof at a magnification of 50× using an electron microscope (such as the Model VE7800 manufactured by Keyence Corp.). The reason for freezing the sample absorbent article is to prevent fluctuations in the thickness dimension attributable to compression of the sample absorbent article when cutting with the razor blade.

(3) The number of the indentations 60 per unit surface area in the central portion of the absorbent article 1 located roughly in the center in the direction of length and width thereof is made to be less than the number of the indentations 70 per unit surface area in the peripheral portion around the central portion, and the size in the planar direction of the indentations 60 in the central portion is made to be greater than the size in the planar direction of the indentations 70 in the peripheral portion. As a result, in an absorbent article in which indentations are formed by embossing, the central portion of the absorbent article 1 that absorbs liquid of a wearer can be made thicker in the center, while the peripheral portion of the absorbent article 1 can be made thinner. Moreover, the central portion of the absorbent article 1 can be given a soft feel to improve the sensation felt by a wearer when wearing the absorbent article 1, while the peripheral portion can be made to have durability. In addition, in the absorbent article 1 having a centrally thick structure in which indentations are formed by embossing, together with being able to fix the crushed pulp layer at a location of high weight of the central portion, a soft sensation can be imparted. Moreover, since the indentations 60 have a large size in the planar direction, they can serve as guides for attaching the absorbent article 1 at a correct location.

(4) The indentations 71, which are formed by compressing the top sheet 10, the side sheet 40 and the absorbent 30 in the thickness direction, are made to be present in the vicinity of the ends in the lengthwise direction of areas where the side sheet 40 overlaps the top sheet 10 and the absorbent 30. As a result, twisting of the absorbent article 1 caused by long-term use can be further inhibited. Moreover, in the case of providing the absorbent article with wings extending in the widthwise direction, a portion of the absorbent is bent when wrapping the wings around an undergarment, thereby making it possible to reduce breakage of the adsorbent.

(5) The crushed pulp layer 34 is provided adjacent to the top sheet 10. As a result, since crushed pulp around the pins that have penetrated the crushed pulp easily moves to the side to facilitate formation of the indentations during embossing, deep indentations can be formed. Consequently, the top sheet 10, the crushed pulp layer 34 and the airlaid layer 32 are firmly fixed even in the case the absorbent 30 has absorbed liquid of the wearer and become wet, thereby making it possible to enhance durability of the absorbent article 1 when used for a long period of time.

(6) The indentations 60 and 70 (71) are arranged in a staggered pattern. As a result, areas surrounded by four indentations 60 and 70 are raised up, thereby further enhancing the soft feel of the absorbent article 1. In addition, the raised areas formed by being surrounded by the indentations 60 and 70 can be made to be uniformly present in the absorbent article 1, thereby inhibiting uneven distribution of rigidity of the absorbent article 1.

Some variations of the absorbent article 1 in accordance with some embodiments of the present invention will be indicated below.

(1) In the absorbent article 1 of an embodiment as described above, the size in the planar direction of the airlaid layer 32 is the same as the size in the planar direction of the crushed pulp layer 34. However, as shown in an absorbent article 1A of FIG. 5, the size in the planar direction of a crushed pulp layer 34A may be smaller than the size in the planar direction of an airlaid layer 32A, an area in the planar direction of the crushed pulp layer 34A may be included in an area in the planar direction of the airlaid layer 32A (i.e., in plane view, the crushed pulp layer 34A is entirely within the boundary of the airlaid layer 32A), and the airlaid layer 32A may be made to extend to both ends of the absorbent article 1A in the lengthwise direction thereof. Since more liquid of a wearer is absorbed by the crushed pulp layer 34A having a small size in the planar direction than the airlaid layer 32A, by employing the configuration described above, dispersion of liquid of the wearer in the planar direction can be inhibited. Twisting of the absorbent article 1A resulting from long-term use can also be inhibited. In addition, since the ends of the absorbent article 1A in the lengthwise direction thereof (rounded sealing portions 80A in FIG. 5) can be made to be thick, the skin does not become painful even if the ends of the absorbent article 1A in the lengthwise direction thereof curl up and contact the skin during use.

Figure 5:
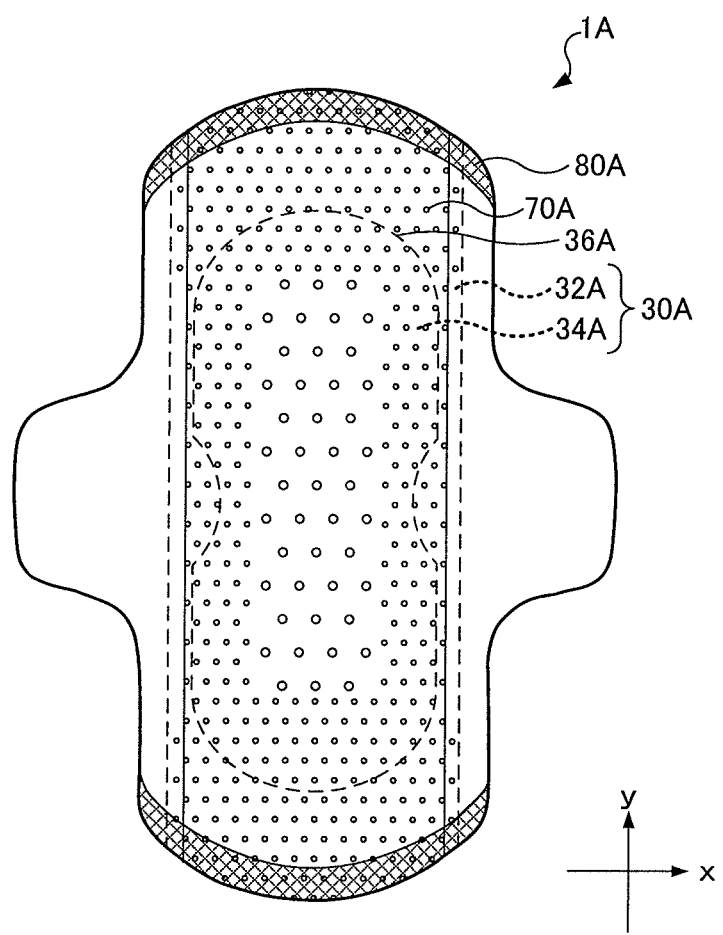
FIG. 5 is a drawing explaining a variation of an absorbent article in an embodiment of the present invention.

(2) As shown in the adsorbent article 1A of FIG. 5, the area in the planar direction of the crushed pulp layer 34A may be included in the area in the planar direction of the airlaid layer 32A, the sides of the airlaid layer 32A in the widthwise direction may be parallel, and the sides of the crushed pulp layer 34A in the widthwise direction may be made to be curved inward. As a result, in the same manner as described above, dispersion of liquid of a wearer in the planar direction can be inhibited, and discomfort in the crotch of the wearer can be suppressed or eliminated.

(3) As shown in the absorbent article 1A of FIG. 5, the rounded sealing portions 80A may be formed on both ends of the absorbent article 1A in the lengthwise direction thereof, and indentations 70A may be formed by embossing on the rounded sealing portions 80A as well. The rounded sealing portions refer to portions where a top sheet, a side sheet, an absorbent and a back sheet are heat-sealed in order to join them together. As a result, twisting of the absorbent article 1A caused by long-term use can be further inhibited.

(4) As shown in the absorbent article 1A of FIG. 5, a plurality of the indentations 70A may be formed in the absorbent 30A along a boundary 36A of the crushed pulp layer 34A. Since the boundary 36A of the crushed pulp layer 34A is where the density of the absorbent 30A changes suddenly, the boundary 36A may serve as an origin of bending for the absorbent article 1A. However, by providing the indentations 70A in the absorbent 30A as previously described, the degree of the change in density of the absorbent 30A at the boundary 36A can be alleviated, thereby making it possible to inhibit the boundary 36A from serving as an origin of bending for the absorbent article 1A.

(5) The size in the planar direction of the crushed pulp layer may be larger than the size in the planar direction of the airlaid layer, and the area in the planar direction of the airlaid layer may be included in the area in the planar direction of the crushed pulp layer (i.e., in plan view, the airlaid layer is entirely within the boundary of the crushed pulp layer). As a result, the absorption of the absorbent can be controlled in the direction that enhances absorbency. In addition, since the soft crushed pulp layer expands in the lengthwise and widthwise directions beyond the more rigid airlaid layer, discomfort in the crotch of a wearer can be suppressed or eliminated. Moreover, since durability of the absorbent article is not required to a great extent for wearers not required to use the absorbent article for a long period of time, an absorbent article for use by wearers not required to use the absorbent article for a long period of time can be controlled so as to reduce the rigidity and enhance the softness of the absorbent.

Figure 6:
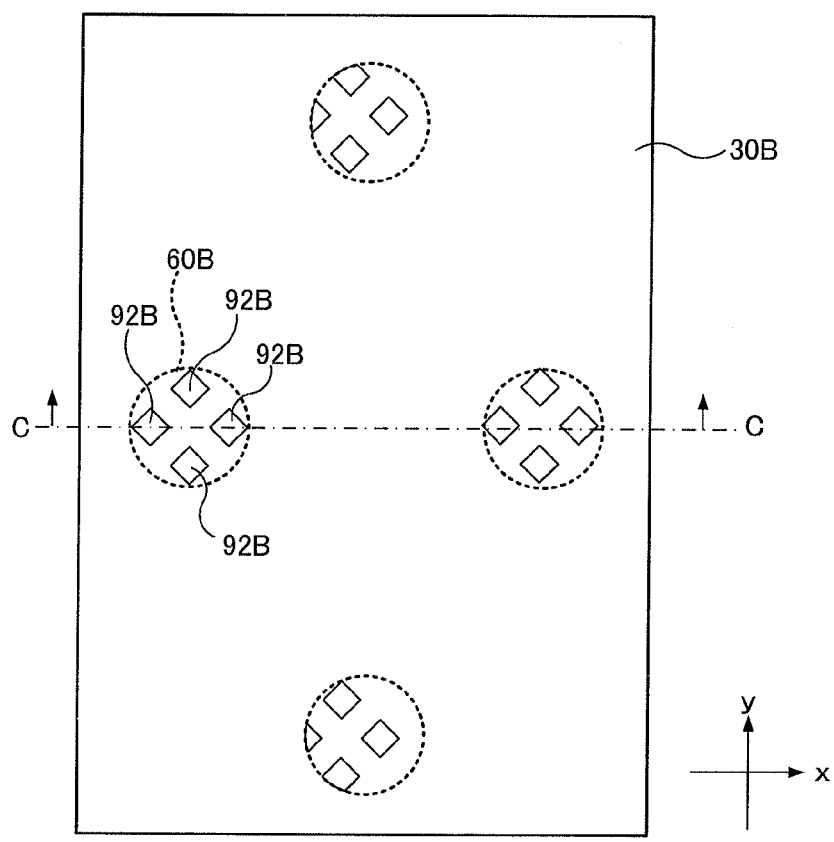
FIG. 6 is a drawing explaining indentations, highly compressed portions and lowly compressed portions provided in a variation of an absorbent article in an embodiment of the present invention.
Figure 6:
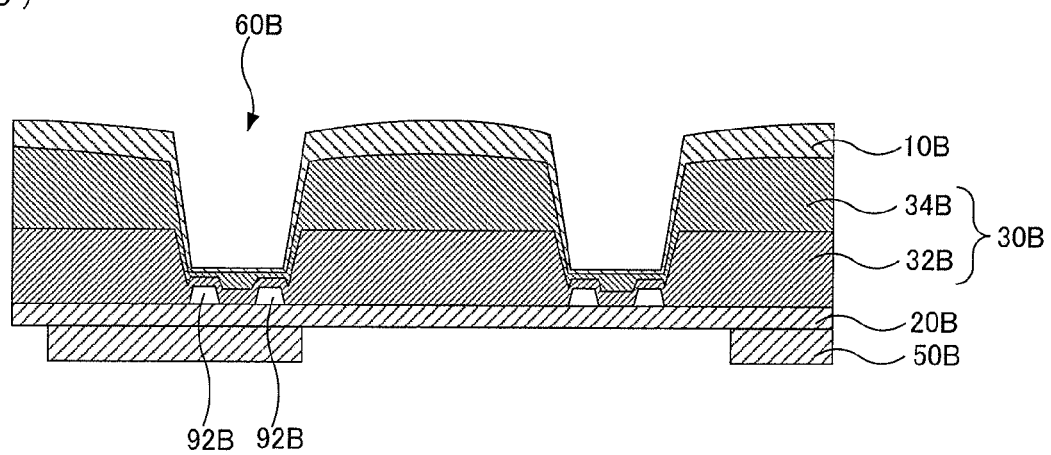

(6) In the absorbent article 1 of an embodiment as described above, the more compressed portions 62 and the less compressed portions 64, which have different depths in the thickness direction, are provided in at least some of the indentations 60 among the plurality of indentations 60 and 70. However, as shown in FIG. 6, compressed portions 92B may be provided at locations opposing a plurality of indentations 60B on the back sheet side of an absorbent 30B. FIG. 6(a) is an overhead view of the compressed portions 92B, while FIG. 6(b) is a cross-sectional view taken along line C-C in FIG. 6(a). As a result, a density gradient can be formed in the absorbent 30B in the bottom portions of the indentations 60B, thereby improving absorption of fluid of a wearer of the absorbent article. In addition, since there are no surface irregularities in the bottom surface inside the indentations 60B, even a highly viscous liquid of the wearer can be satisfactorily absorbed. Furthermore, the compressed portions 92B may also be provided at only some, not all, of the locations opposing the plurality of indentations 60B on the back sheet side of the absorbent 30B.

Figure 7:
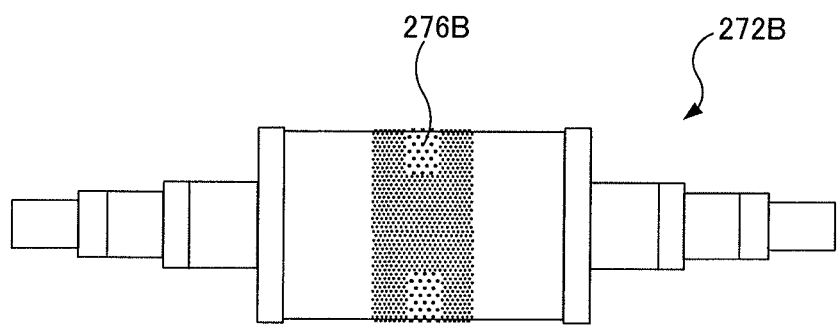
FIG. 7 is a drawing explaining an upper roller of an embossing device used for forming indentations provided in a variation of an absorbent article in an embodiment of the present invention.
Figure 7:
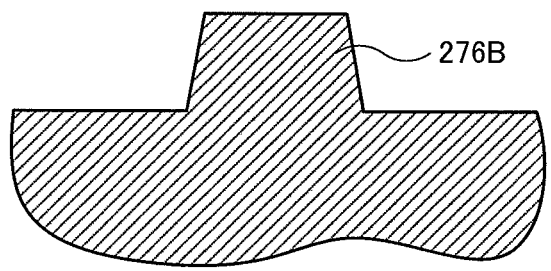
Figure 8:
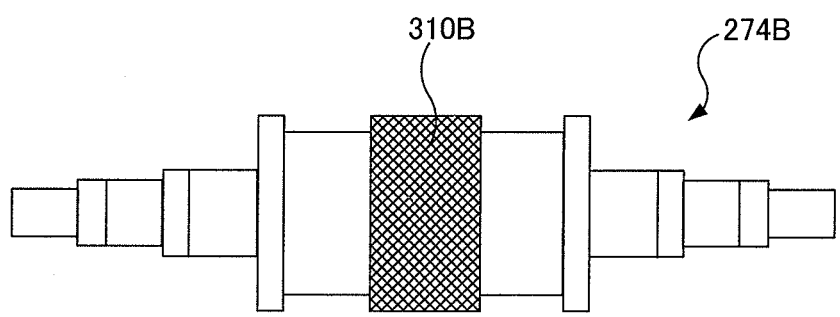
FIG. 8 is a drawing explaining a lower roller of an embossing device for forming highly compressed portions and lowly compressed portions provided in a variation of an absorbent article in an embodiment of the present invention.
Figure 8:
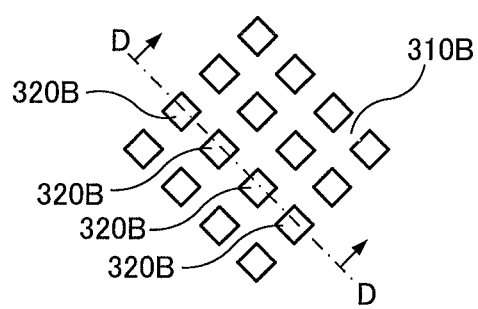
Figure 8:
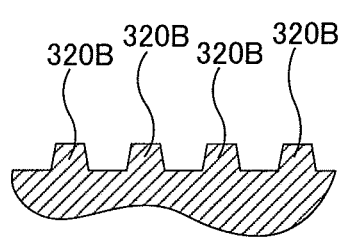

The following provides an explanation of an upper roller and a lower roller of an embossing device for forming the compressed portions 92B in the absorbent 30B and forming the indentations 60B in the top sheet 10B and the absorbent 30B with reference to FIGS. 7 and 8. FIG. 7(a) is a drawing showing an upper roller, while FIG. 7(b) is a cross-sectional view of a pin provided on the upper roller. As shown in FIG. 7(a), pins 276B are provided on an upper roller 272B at locations corresponding to indentations to be provided in the absorbent article. As shown in FIG. 7(b), the shape of the pins is flat with the exception of a conical tip. Differing from the upper roller 272 of the embossing device 270 used in absorbent article 1 of an embodiment, the projections 278 for forming highly compressed portions of indentations are not provided on the tips of the pins 276B.

FIG. 8(a) is a drawing showing a lower roller, FIG. 8(b) is a drawing showing the details of lattice-like grooves provided in the lower roller, and FIG. 8(c) is a cross-sectional view taken along line D-D in FIG. 8(b). As shown in FIG. 8(a), lattice-like grooves 310B are provided in a lower roller 274B. As shown in FIGS. 8(b) and 8(c), projections 320B, having a flat shape with the exception of a pyramid-shaped tip having a square top, are formed by the lattice-like grooves 310B. In comparison with the projections 278 provided on the tips of the pins of the upper roller 272 of the embossing device 270 used in the absorbent article 1 in an embodiment, the projections 320B are not chipped or worn down since they are uniformly provided on the lower roller 274B. Furthermore, compressed portions 92B may be also formed by using a lower roller on which projections 320B, having a cross-section in the planar direction in the shape of a polygon other than a circle or square, are uniformly provided.

(7) Although the absorbent article 1 of an embodiment as described above is in the form of a sanitary napkin, further embodiments of the present invention can also be applied to other absorbent articles such as a panty liner, incontinence pad or incontinence liner. Embodiments of the present invention are particularly preferably applied to a absorbent article with a total thickness in a central region in an uncompressed state of less than 4 mm.

One or more embodiments and variations can be combined. Variations can also be combined in any manner.

The above description has been provided as examples only, the invention is not limited in any way to the aforementioned embodiment.

This application claims the benefit of Japanese Application No. 2010-223059 the entire disclosure of which is incorporated by reference herein.

BRIEF DESCRIPTION OF THE REFERENCE SYMBOLS

1 Absorbent article
10 Top sheet
20 Back sheet
30 Absorbent
32 Airlaid layer
34 Crushed pulp layer
40 Side sheets
50 Pressure-sensitive adhesive portion
60,70,71 Indentation
62 Highly compressed portion
64 Lowly compressed portion
210 Airlaid non-woven fabric roller
220 Pattern drum
240 Absorbent front and back-cutting cutter
250 Top sheet roller
260 Side sheet roller
270 Embossing device
272 Upper roller
274 Lower roller
280 Back sheet roller
290 Cutter

The invention claimed is:

1. An absorbent article, comprising:
a liquid-permeable top sheet,
a liquid-impermeable back sheet opposing the top sheet,
an absorbent provided between the top sheet and the back sheet, and
a side sheet provided on each side of the top sheet in a widthwise direction of the absorbent article, and having an area that overlaps the top sheet and the absorbent; wherein
the absorbent contains an airlaid layer, formed by joining fibers with a binder, and a crushed pulp layer,
the crushed pulp layer is provided on a top sheet side of the absorbent,
the airlaid layer is provided on a back sheet side of the absorbent, and
the absorbent article has a plurality of compressed pin-shaped indentations extending through the side sheet and the top sheet and into the absorbent in a thickness direction of the absorbent article, and a plurality of compressed pin-shaped indentations extending through the top sheet and into the absorbent in the thickness direction.

2. The absorbent article according to claim 1, wherein
at least some of the indentations include more compressed portions and less compressed portions having different depths in the thickness direction, and
a depth of the more compressed portions in the thickness direction is greater than a depth of the less compressed portions in the thickness direction.

3. The absorbent article according to claim 1, wherein
a number of the indentations per unit surface area in a central portion of the absorbent article located in the center in both a lengthwise direction and the widthwise direction of the absorbent article is less than a number of the indentations per unit surface area in a peripheral portion around the central portion, and/or
a size in a planar direction of the indentations in the central portion is greater than the size in the planar direction of the indentations in the peripheral portion.

4. The absorbent article according to claim 1, wherein the compressed indentations, which are extending through the side sheet, the top sheet and into the absorbent in the thickness direction, are present in the vicinity of the ends in a lengthwise direction of the area where the side sheet overlaps the top sheet and the absorbent.

5. The absorbent article according to claim 1, wherein
in a planar direction of the absorbent article, the crushed pulp layer overlaps an area of the airlaid layer, and
the airlaid layer extends to both ends of the absorbent article in a lengthwise direction thereof.

6. The absorbent article according to claim 5, wherein at least some of the indentations are positioned in a boundary extending between an area that includes the airlaid layer and the crushed pulp layer and an area that includes the airlaid layer but not the crushed pulp layer.

7. The absorbent article according to claim 1, wherein
an area in a planar direction of the absorbent article of the crushed pulp layer overlaps the airlaid layer,
sides of the airlaid layer in the widthwise direction are parallel, and/or
sides of the crushed pulp layer in the widthwise direction are curved inward.

8. The absorbent article according to claim 1, wherein the crushed pulp layer is provided adjacent to the top sheet.

9. An absorbent article as claimed in claim 1, wherein at least some of the indentations extend from the top sheet through the crushed pulp layer to the airlaid layer and fix the top sheet to the airlaid layer.

10. An absorbent article as claimed in claim 1, wherein at least some of the indentations extend through the side sheet, the top sheet and the crushed pulp layer to the airlaid layer and fix the side sheet to the airlaid layer.

11. An absorbent article as claimed in claim 1, wherein a maximum thickness of the absorbent article is less than 4 mm.

12. The absorbent article according to claim 1, wherein a distance in a planar direction between two adjacent indentations is from 3 to 20 mm.

13. The absorbent article according to claim 1, wherein a diameter in a planar direction of each indentation is from 0.5 to 6.0 mm.

14. The absorbent article according to claim 1, wherein a ratio of a total surface area of all indentations in a planar direction to a total surface area of the absorbent article in the planar direction is from 3 to 30%.

15. The absorbent article according to claim 1, wherein a ratio of a total surface area of all indentations in a planar direction to a total surface area of the absorbent article in the planar direction is from 5 to 10%.

16. The absorbent article according to claim 1, wherein an area in a planar direction of the airlaid layer is included in an area in the planar direction of the crushed pulp layer.

17. The absorbent article according to claim 1, wherein the absorbent further includes, on the back sheet side thereof, compressed portions at locations opposing at least some of the indentations.

18. The absorbent article according to claim 17, wherein bottom surfaces of the indentations opposing the compressed portions are free of irregularities.

19. The absorbent article according to claim 1, wherein an area in a planar direction of the crushed pulp layer is included in an area in the planar direction of the airlaid layer.

20. The absorbent article according to claim 1, wherein an area in a planar direction of the crushed pulp layer has the same size as that of an area in the planar direction of the airlaid layer.

21. The absorbent article according to claim 1, wherein the width of the area of the absorbent article where the indentations are formed is narrower roughly in the center in a lengthwise direction of the absorbent article.

22. The absorbent article according to claim 1, wherein the indentations are arranged in a staggered pattern.

23. The absorbent article according to claim 1, wherein rounded sealing portions are formed on both ends of the absorbent article in a lengthwise direction thereof, and at least some of the indentations are embossed on the rounded sealing portions.

* * * * *